United States Patent
Girard et al.

(10) Patent No.: US 9,809,504 B2
(45) Date of Patent: Nov. 7, 2017

(54) PROCESS FOR TRANSFORMATION OF A FEEDSTOCK COMPRISING A LIGNOCELLULOSIC BIOMASS USING AN ACIDIC HOMOGENEOUS CATALYST IN COMBINATION WITH A HETEROGENEOUS CATALYST COMPRISING A SPECIFIC SUBSTRATE

(71) Applicant: IFP Energies Nouvelles, Rueil-Malmaison (FR)

(72) Inventors: Etienne Girard, Lyons (FR); Amandine Cabiac, Givors (FR); Damien Delcroix, Saint-Maurice-L'Exil (FR)

(73) Assignee: IFP ENERGIES NOUVELLES, Rueil-Malmaison (FR)

( * ) Notice: Subject to any disclaimer, the term of this patent is extended or adjusted under 35 U.S.C. 154(b) by 0 days.

(21) Appl. No.: 14/862,296

(22) Filed: Sep. 23, 2015

(65) Prior Publication Data
US 2016/0090331 A1 Mar. 31, 2016

(30) Foreign Application Priority Data

Sep. 26, 2014 (FR) .................... 14 59112

(51) Int. Cl.
| | |
|---|---|
| *C07B 33/00* | (2006.01) |
| *B01J 21/02* | (2006.01) |
| *B01J 21/06* | (2006.01) |
| *B01J 23/24* | (2006.01) |
| *B01J 23/42* | (2006.01) |
| *B01J 23/755* | (2006.01) |
| *B01J 23/34* | (2006.01) |
| *C07C 29/132* | (2006.01) |
| *C07C 29/60* | (2006.01) |
| *C07C 27/04* | (2006.01) |
| *B01J 23/00* | (2006.01) |
| *B01J 23/58* | (2006.01) |
| *B01J 23/78* | (2006.01) |
| *B01J 37/02* | (2006.01) |
| *B01J 37/18* | (2006.01) |
| *B01J 23/656* | (2006.01) |
| *B01J 23/89* | (2006.01) |

(52) U.S. Cl.
CPC ............... *C07B 33/00* (2013.01); *B01J 21/02* (2013.01); *B01J 21/063* (2013.01); *B01J 21/066* (2013.01); *B01J 23/002* (2013.01); *B01J 23/34* (2013.01); *B01J 23/42* (2013.01); *B01J 23/58* (2013.01); *B01J 23/755* (2013.01); *B01J 23/78* (2013.01); *B01J 37/0201* (2013.01); *C07C 27/04* (2013.01); *C07C 29/132* (2013.01); *C07C 29/60* (2013.01); *B01J 23/6562* (2013.01); *B01J 23/8906* (2013.01); *B01J 37/0236* (2013.01); *B01J 37/18* (2013.01); *Y02P 20/52* (2015.11)

(58) Field of Classification Search
CPC ................................ B01J 23/42; C07B 33/00
See application file for complete search history.

(56) References Cited

U.S. PATENT DOCUMENTS

| | | | |
|---|---|---|---|
| 8,618,341 B2 | 12/2013 | Yie et al. | |
| 2009/0326286 A1 | 12/2009 | Yie et al. | |
| 2013/0036660 A1* | 2/2013 | Woods | C10G 3/42 44/307 |

OTHER PUBLICATIONS

Glycerol hydrogenolysis on heterogeneous catalysts Julien Chaminand et al. Green Chem. vol. 6, pp. 359-361, 2004.*
Search Report and Opinion from corresponding French Patent Application No. 14/59112 dated May 13, 2015.
Joseph B. Binder et al. "Simple Chemical Transformation of Lignocellulosic Biomass into Furans for Fuels and Chemicals" Journal of the American Chemical Society, [2009], vol. 131, No. 11, pp. 1979-1985.

\* cited by examiner

*Primary Examiner* — Douglas B Call
(74) *Attorney, Agent, or Firm* — Millen White Zelano and Branigan, PC; John Sopp; Csaba Henter

(57) ABSTRACT

Process for transformation of a feedstock of lignocellulosic biomass and/or the carbohydrates, into mono-oxidized or poly-oxidized compounds, wherein the feedstock is contacted, simultaneously, with a catalytic system that comprises one or more homogeneous catalysts selected from Brønsted acids and heterogeneous catalysts comprising at least one metal selected from groups 6 to 11 and 14 of the periodic table, and a substrate selected from perovskites of formula $ABO_3$, in which A is Mg, Ca, Sr, Ba, and La, and B is selected from Fe, Mn, Ti and Zr, oxides of lanthanum, neodymium, yttrium, cerium, and niobium, or mixtures thereof, and mixed oxides of aluminates of zinc, copper, and cobalt, or mixtures thereof, in the same reaction chamber, with at least one solvent, being water or water with at least one other solvent, under reducing atmosphere, and temperature of 50° C. to 300° C., and pressure of 0.5 MPa to 20 MPa.

14 Claims, No Drawings

PROCESS FOR TRANSFORMATION OF A FEEDSTOCK COMPRISING A LIGNOCELLULOSIC BIOMASS USING AN ACIDIC HOMOGENEOUS CATALYST IN COMBINATION WITH A HETEROGENEOUS CATALYST COMPRISING A SPECIFIC SUBSTRATE

PRIOR ART

For several years, there has been a sharp resurgence of interest for the incorporation of products of renewable origin within fuel and chemical industries, in addition to or in place of products of fossil origin. One possible method is the conversion of the cellulose contained in the lignocellulosic biomass into chemical products or intermediate products, such as products that contain one to six hydroxyl groups, which are n-propanol, ethylene glycol, propylene glycol, glycerol, 1,2-butanediol, or 1,2-hexanediol.

The term lignocellulosic biomass (LCB) or lignocellulose encompasses several components that are present in variable quantities according to the origin thereof: cellulose, hemicellulose, and lignin. Hemicellulose and cellulose constitute the carbohydrate part of the lignocellulose. These are polymers of sugars (pentoses and hexoses). Lignin is a macromolecule that is rich in phenolic units. Lignocellulosic biomass is defined as, for example, the products that are obtained from forestry operations and the sub-products that are obtained from agriculture, such as straw as well as certain dedicated plants with a high agricultural yield, such as Miscanthus or poplar.

The production of chemical products from lignocellulosic biomass makes it possible both to reduce the energy dependency relative to petroleum and to protect the environment through reducing greenhouse gas emissions without using resources intended for food uses.

The direct transformation of a feedstock selected from among lignocellulosic biomass and carbohydrates, by themselves or in a mixture of chemical products or intermediate products, in particular mono-oxidized or poly-oxidized, is a particularly advantageous method. Direct transformation is defined as the transformation of a stage of said feedstock, optionally pretreated, into upgradeable mono-oxidized or poly-oxidized products.

The upgrading of the lignocellulosic biomass or the cellulose contained in the biomass by the use of a combination of homogeneous and heterogeneous catalysts is extensively described in the literature.

In particular, the use of a combination of homogeneous catalysts based on Brønsted acids and heterogeneous catalysts has often been described for the transformation of the lignocellulosic biomass or the cellulose.

The patent application WO2013/015990 describes a process for producing polyols and in particular alcohols, organic acids, aldehydes, monosaccharides, polysaccharides, phenolic compounds, carbohydrates, glycerol, proteins and depolymerized lignin as well as hydrocarbons by the hydrolysis and the hydrogenation of microcrystalline celluloses, paper pulp and glucose, in the presence of a catalytic system that comprises a non-supported compound based on tungsten or molybdenum, by itself or in a mixture, and a supported compound based on Pt, Pd, Ru, Rh, Ni, Ir by itself or in a mixture on a solid substrate that is selected from among carbon, $Al_2O_3$, $ZrO_2$, $SiO_2$, MgO, $Ce_xZr_yO_2$, $TiO_2$, SiC, silica-alumina, clays and zeolites taken by themselves or in a mixture. The non-supported compounds, based on tungsten or molybdenum, by themselves or in a mixture, are the Brønsted acids that are selected from among tungstic acid, molybdic acid, ammonium metatungstate, and the heteropolyanions of tungsten, molybdenum, tungstic acid, and molybdic acid, by itself or in a mixture. Said process makes possible the conversion of cellulose into ethylene glycol or into propylene glycol with a high yield and good selectivity. In the examples illustrating the invention, the non-supported catalysts are the following Brønsted acids: tungstic acid ($H_2WO_4$), phosphotungstic acid ($H_3PW_{12}O_{40}$) and ammonium metatungstate (($NH_4)_6(W_{12}O_{40}).xH_2O$). The supported catalyst is Ni/norite CA-1 or Pd/C, with the metal contents being between 0.6 and 5% by weight. The majority products obtained in these examples are ethylene glycol and propylene glycol. The transformation of cellulose is carried out in water at a content of 1% by weight of cellulose/water at 245° C. at 60 bar of $H_2$ (at ambient temperature).

The patent application US2009/0326286 describes the hydrolysis and hydrogenation of lignocellulosic biomasses into monosaccharides in the presence of a homogeneous catalyst and a heterogeneous catalyst. The homogeneous catalyst is described as a Brønsted mineral or organic acid preferably selected from among the following acids: $H_2SO_4$, $H_3PO_4$, $H_3PO_3$, $H_3PO_2$ and $CH_3COOH$. The heterogeneous catalyst is based on activated carbon or alumina, on which is deposited a transition metal that is selected from among ruthenium, nickel, platinum, and palladium at contents of between 0.1% and 5.5% by weight relative to the total mass of the heterogeneous catalyst. The formed products and the associated yields are not specified.

Sels et al. (Chem. Commun. 2010, 46, 3577-3579) study the transformation of cellulose into hexitols (sorbitol+mannitol) in the presence of a homogeneous catalyst and a heterogeneous catalyst. The homogeneous acid catalysts that are used are the Brønsted acids $H_2SO_4$ and $H_4SiW_{12}O_{40}$. The heterogeneous catalyst is 5% by weight of Ru/C. The conversion of the microcrystalline cellulose is respectively 50% and 80% with these two acids for a reaction in water at 190° C. and at 50 bar of $H_2$ for 24 hours ($pH_{(25° C.)}=2$). The associated yields of hexitols are 13% and 48%. The ground cellulose is solubilized more quickly with a total conversion in 1 hour under the same operating conditions and a hexitol yield of 87%.

With a slightly different perspective, Zhang et al. (Chem. Commun., 2012, 48, 7052-7054) combines tungstic acid $H_2WO_4$, water-insoluble at ambient temperature, and the heterogeneous catalyst, 5% by weight of Ru/C, for the conversion of cellulose into ethylene glycol in water at 245° C. at 60 bar of $H_2$ (at ambient temperature). The special feature of this system is that tungstic acid solubilizes when hot and switches from heterogeneous to homogeneous during the temperature rise to 245° C. The ethylene glycol yield reaches 59% with total conversion of cellulose in 30 minutes.

More recently, C. Liang (Green Chem., 2013, 15, 891-895) described a combination of catalysts for the production of ethylene glycol from cellulose, in water at 245° C. at 60 bar of $H_2$. The addition of calcium hydroxide $Ca(OH)_2$ in association with the heterogeneous catalyst CuCr makes it possible to increase the ethylene glycol yield of the reaction from 5% to 30%. For its part, the propylene glycol yield remains stable around 30-35%.

The patent application US2011/0060148 of BIOeCON International Holding describes a process for conversion of lignocellulosic biomass into polyols, making it possible to obtain a high polyol yield and to minimize the formation of by-products. In particular, the process comprises a stage for hydrolysis of cellulose and lignocellulosic biomasses into glucose, a stage for hydrogenation of the glucose formed into sorbitol, a stage for dehydration of polyols obtained, and a stage for recovery, with said stages being carried out in a hydrated metal salt used as a solvent according to a hydrated metal salt/lignocellulosic biomass ratio of between 1 and 50, which corresponds to a lignocellulosic biomass/metal salt ratio of between 0.02 and 1. The hydrolysis of the cellulose is carried out in a hydrated metal salt, used as a solvent, selected from among halides of zinc, calcium, and lithium, by themselves or in a mixture, and in particular in $ZnCl_2.4H_2O$, used as a solvent. The hydrolysis stage is also performed in the presence of an inorganic acid, preferably hydrochloric acid (HCl). The hydrogenation of glucose is also carried out in said hydrated metal salt, used as a solvent, in the presence of an inorganic acid, preferably hydrochloric acid (HCl), and a heterogeneous catalyst that is selected from among the conventional catalysts for hydrogenation of sugars, such as the catalysts Ru/C, Raney nickel, Raney copper, and nickel on a carbon or alumina substrate and preferably in the presence of Ru/C, without detailing the metal content by mass. The examples illustrate the use as solvent of the hydrated inorganic salt $ZnCl_2.4H_2O$ in a $ZnCl_2.4H_2O$/cellulose ratio by mass of 12/1. The maximum conversion of the thus obtained cellulose after 1.5 hours is 100%.

Finally, in 2009, R. Raines (JACS, 2009, 131, 1979-1985) described the transformation of sugars, cellulose, and lignocellulose into 2,5-dimethylfuran in two stages. The first stage is carried out in an ionic liquid medium based on dimethylacetamide-LiCl/[EMIM]Cl ([EMIM][Cl]=1-ethyl-3-methyl imidazolium chloride) at 140° C. for 2 hours and is catalyzed by a mixture of the metal salt of chromium trichloride ($CrCl_3$) and hydrochloric acid (HCl), both at 10 mol % relative to cellulose. At the end of this first stage, a stage for purification by steric exclusion chromatography is implemented and makes it possible to eliminate the chloride ions from the medium in such a way as to prevent the poisoning of the catalyst used in the second stage. The second stage can thus take place and involves the transformation of the purified solution in the presence of a copper-based catalyst deposited on Ru/C under hydrogen, in 1-butanol at 220° C. for 10 hours for forming 2,5-dimethylfuran. The thus described two-stage process makes it possible to obtain a high selectivity of 2,5-dimethylfuran but also leads to the production of a significant amount of humins.

There is no process described in the literature that makes possible a direct transformation of a feedstock that is selected from among the lignocellulosic biomass and the carbohydrates, by themselves or in a mixture, into upgradeable mono-oxidized or poly-oxidized products, by bringing into contact said feedstock, simultaneously, within the same reaction medium, with a combination of at least one homogeneous catalyst that is selected from among the inorganic Brønsted acids and organic Brønsted acids, and one or more heterogeneous catalysts comprising a specific substrate that is selected from among the perovskites of general formula $ABO_3$, in which A is selected from among the elements Mg, Ca, Sr and Ba, and La, and B is selected from among the elements Fe, Mn, Ti and Zr, the oxides of the elements selected from among lanthanum (La), neodymium (Nd) and yttrium (Y), cerium (Ce) and niobium (Nb), by themselves or in a mixture, and the mixed oxides that are selected from among the aluminates of zinc (Zn), copper (Cu), and cobalt (Co), by themselves or in a mixture, of the type of those described in this invention.

The works of the applicant made it possible to demonstrate that, surprisingly enough, bringing a feedstock that is selected from among the lignocellulosic biomass and the carbohydrates, by themselves or in a mixture, simultaneously, into contact with at least one homogeneous catalyst and one or more heterogeneous catalysts, as claimed, in the same reaction chamber that operates under specific operating conditions made it possible to obtain upgradeable mono-oxidized or poly-oxidized products directly and to reduce the content of non-upgradeable products, such as humins.

Furthermore, the heterogeneous catalytic system that is used according to the invention has the advantage of being stable under reaction conditions in contrast to the refractory oxides such as the oxides of aluminum or silicon, for example.

SUMMARY OF THE INVENTION

One object of this invention is therefore to provide a process for transformation of a feedstock that is selected from among the lignocellulosic biomass and the carbohydrates, by themselves or in a mixture, into mono-oxidized or poly-oxidized compounds, in which said feedstock is brought into contact, simultaneously, with a catalytic system that comprises one or more homogeneous catalysts and one or more heterogeneous catalysts, in the same reaction chamber, in the presence of at least one solvent, with said solvent being water by itself or in a mixture with at least one other solvent, under a reducing atmosphere, and at a temperature of between 50° C. and 300° C., and at a pressure of between 0.5 MPa and 20 MPa, in which Said homogeneous catalyst or catalysts is/are selected from among the inorganic Brønsted acids and the organic Brønsted acids.

Said heterogeneous catalyst or catalysts comprise(s) at least one metal that is selected from among the metals of groups 6 to 11 and the metals of group 14 of the periodic table, and a substrate that is selected from among the perovskites of general formula $ABO_3$, in which A is selected from among the elements Mg, Ca, Sr, Ba, and La, and B is selected from among the elements Fe, Mn, Ti and Zr, the oxides of elements selected from among lanthanum (La), neodymium (Nd) and yttrium (Y), cerium (Ce) and niobium (Nb), by themselves or in a mixture, and the mixed oxides that are selected from among the aluminates of zinc (Zn), copper (Cu), and cobalt (Co), by themselves or in a mixture.

In this invention, reference is made to the new notation of the periodic table: Handbook of Chemistry and Physics, 76th Edition, 1995-1996.

In this invention, homogeneous catalyst is defined as a catalyst that is soluble under the operating conditions of the reaction. Heterogeneous catalyst is defined as a catalyst that is insoluble under the operating conditions of the reaction.

One advantage of this invention is to make it possible to obtain the upgradeable mono-oxidized or poly-oxidized products directly while limiting the formation of non-upgradeable products such as soluble and insoluble humins, i.e., products of high molecular weight that are obtained from undesirable condensations of sugars and their derivatives.

Another advantage of this invention resides in the use of a specific heterogeneous catalyst that exhibits the advantage of being stable under the reaction conditions in contrast to the refractory oxides such as the oxides of aluminum or silicon, for example.

In the case where the treated feedstock is a solid feedstock, i.e., preferably selected from among the lignocellulosic biomass or cellulose, another advantage of this invention is to make possible both the increase in the maximum conversion and the acceleration of the conversion kinetics of the lignocellulosic biomass or the cellulose by the simultaneous use in the same reaction chamber, operating under a reducing atmosphere, of the combination of at least one homogeneous catalyst and of one or more heterogeneous catalyst(s) as claimed.

DETAILED DESCRIPTION OF THE INVENTION

The Feedstock

The feedstock that is treated in the process according to the invention is a feedstock that is selected from among the lignocellulosic biomass and the carbohydrates, by themselves or in a mixture, with the carbohydrates preferably being selected from among polysaccharides, oligosaccharides and monosaccharides, by themselves or in a mixture.

We define polysaccharides as one or more compounds that contain at least 10 subunits of oses linked covalently.

The preferred polysaccharides that are used as a feedstock in this invention are selected from among starch, inulin, cellulose and hemicellulose, by themselves or in a mixture.

We define oligosaccharides as one or more compounds containing from two to ten subunits of oses linked covalently.

More particularly, oligosaccharide refers to, on the one hand, a carbohydrate that has as its formula $(C_6H_{10}O_5)_n$ or $C_{61}H_{10n+2}O_{5n+1}$ where n is an integer greater than 1, obtained by partial hydrolysis of starch, inulin, lignocellulosic biomass, cellulose and hemicellulose, and, on the other hand, a so-called mixed carbohydrate that has as its composition $(C_6H_{10}O_5)_m(C_5H_8O_4)_n$, $(C_{6m}H_{10m+2}O_{5m+1})(C_{5n}H_{8n+2}O_{4n+1})$ where m and n are integers that are greater than or equal to 1.

The oligosaccharides are preferably selected from among the oligomers of pentoses and/or hexoses with a degree of polymerization that is less than that of cellulose and hemicellulose (2-30). They can be obtained by partial hydrolysis of starch, inulin, lignocellulosic biomass, cellulose, or hemicellulose. The oligosaccharides are in general water-soluble.

The preferred oligosaccharides that are used as a feedstock in this invention are selected from among saccharose, lactose, maltose, isomaltose, inulobiose, melibiose, gentiobiose, trehalose, cellobiose, cellotriose, cellotetraose and the oligosaccharides that are obtained from the hydrolysis of polysaccharides named in the preceding paragraph.

Monosaccharides refer to simple sugars (hexoses, pentoses) that can be produced by complete or partial depolymerization of polysaccharides.

The preferred monosaccharides that are used as a feedstock in this invention are selected from among glucose, galactose, mannose, fructose, and altrose.

The lignocellulosic biomass essentially consists of three natural components that are present in variable quantities according to the origin thereof: cellulose, hemicellulose, and lignin.

Cellulose $(C_6H_{10}O_5)_n$ represents the major portion (40-60%) of the composition of the lignocellulosic biomass. Cellulose is a linear homopolymer that consists of numerous units of D-anhydroglucopyranose (AGU) that are connected to one another by glycosidic bonds β-(1→4). The repetition unit is the cellobiose dimer.

Cellulose is insoluble in water at ambient temperature and pressure.

The cellulose that is used can be crystalline or amorphous.

Hemicellulose is the second carbohydrate after cellulose in terms of quantity and constitutes 20 to 40% by weight of the lignocellulosic biomass. In contrast to cellulose, this polymer consists for the most part of monomers of pentoses (cycles with 5 atoms) and hexoses (cycles with 6 atoms). Hemicellulose is an amorphous heteropolymer with a degree of polymerization that is less than that of cellulose (30-100).

Lignin is an amorphous macromolecule that is present in the lignocellulosic compounds in variable proportions according to the origin of the material (straw ~15%, wood: 20-26%). Its function is mechanical reinforcement, hydrophobization, and the support of plants. This macromolecule that is rich in phenolic units can be described as resulting from the combination of three monomer units of the propyl-methoxy-phenol type. Its molar mass varies from 5,000 g/mol to 10,000 g/mol for hardwoods and reaches 20,000 g/mol for softwoods.

The lignocellulosic raw material can advantageously consist of wood or plant waste. Other nonlimiting examples of lignocellulosic biomass material are waste from agricultural operations, such as, for example, straw, grasses, stems, pits, or shells; waste from forestry operations, such as initial cutting products, bark, sawdust, chips, or scraps; products from forestry operations; dedicated crops (short-rotation shrubs); waste from the food-processing industry, such as waste from the industry of cotton, bamboo, sisal, banana, corn, switchgrass, alfalfa, coconut, or bagasse; household organic waste; waste from wood transformation plants, and scrap wood from construction, paper pulp, paper, which may or may not be recycled.

The lignocellulosic biomass can advantageously be used in its raw form, i.e., in its entirety from these three cellulose, hemicellulose and lignin components. The raw biomass generally comes in the form of fibrous residues or powder. It can also advantageously be ground or shredded to make possible its transport.

The lignocellulosic biomass feedstock can advantageously also be used in its pretreated form, i.e., in a form that contains at least one cellulosic portion after extraction of lignin and/or hemicellulose.

The biomass preferably undergoes a pretreatment so as to increase the reactivity and the accessibility of the cellulose within the biomass before its transformation. These pretreatments are of a mechanical, thermochemical, thermal-mechanical-chemical and/or biochemical nature, and bring about the decrystallization of the cellulose, a reduction of the degree of polymerization of the cellulose, the solubilization of hemicellulose and/or lignin and/or cellulose, or the partial hydrolysis of hemicellulose and/or cellulose following the treatment.

The pretreatment makes it possible to prepare the lignocellulosic biomass by separating the carbohydrate part of the lignin and by adjusting the size of the biomass particles that are to be treated. The size of the biomass particles after pretreatment is generally less than 5 mm, preferably less than 500 microns.

The Catalysts

In accordance with the invention, said feedstock is brought into contact in the process according to the invention, simultaneously, with a catalytic system that comprises one or more homogeneous catalysts and one or more heterogeneous catalysts as claimed, in the same reaction chamber, in the presence of at least one solvent, with said solvent being water by itself or in a mixture with at least one other solvent, under reducing atmosphere, and at a temperature that is between 50° C. and 300° C., and at a pressure of between 0.5 MPa and 20 MPa.

Preferably, said feedstock is brought into contact in the process according to the invention, simultaneously, with a catalytic system that consists of one or more homogeneous catalysts and one or more heterogeneous catalysts as claimed.

An essential criterion of this invention resides in bringing said feedstock into contact, under the operating conditions as claimed, simultaneously, with a combination of one or more homogeneous catalysts and one or more heterogeneous catalysts as claimed, within the same reaction chamber.

Actually, the reactions involved in the process for transformation of said feedstock are not successive reactions because of the use and the simultaneous operation of a combination of at least one homogeneous catalyst as claimed and one or more heterogeneous catalysts, in the same reaction chamber.

The conversion of the feedstock induced by the homogeneous catalyst or catalysts and the transformation of the products that are thus dissolved by the heterogeneous catalyst or catalysts is therefore done in a concomitant and complementary manner. It is thus possible to take advantage of this compatibility between the homogenous and heterogeneous catalysts to avoid any intermediate work of treatment or purification, synonymous with additional process costs and significant material losses associated with this stage. Preferably, said process according to the invention is not performed in two successive stages.

In accordance with the invention, said homogenous catalyst(s) is (are) selected from among the inorganic Brønsted acids and the organic Brønsted acids.

Preferably, the inorganic Brønsted acids are selected from among, without being limited to, the following inorganic acids: HF, HCl, HBr, HI, $H_2SO_3$, $H_2SO_4$, $H_3PO_2$, $H_3PO_4$, $HNO_2$, $HNO_3$, $H_2WO_4$, $H_4SiW_{12}O_{40}$, $H_3PW_{12}O_{40}$, $(NH_4)_6(W_{12}O_{40}).xH_2O$, $H_4SiMo_{12}O_{40}$, $H_3PMo_{12}O_{40}$, $(NH_4)_6Mo_7O_{24}.xH_2O$, $H_2MoO_4$, $HReO_4$, $H_2CrO_4$, $H_2SnO_3$, $H_4SiO_4$, $H_3BO_3$, $HClO_4$, $HBF_4$, $HSbF_5$, $HPF_6$, $H_2FO_3P$, $ClSO_3H$, $FSO_3H$, $HN(SO_2F)_2$ and $HIO_3$.

In a preferred manner, the inorganic Brønsted acids are selected from among the following inorganic acids: HCl, $H_2SO_4$, $H_3PO_4$, $H_2WO_4$, $H_2MoO_4$, $HReO_4$, $H_2CrO_4$.

A very preferred inorganic Brønsted acid homogeneous catalyst is selected from among tungstic acid $H_2WO_4$, hydrochloric acid HCl, and sulfuric acid $H_2SO_4$. In a very preferred manner, the inorganic Brønsted acid homogeneous catalyst is tungstic acid $H_2WO_4$. It can also be denoted $WO_3.H_2O$, or $WO_3.xH_2O$, with x between 1 and 20, x being variable as a function of the degree of hydration of tungsten oxide $WO_3$.

Preferably, the organic Brønsted acids are selected from among, without being limited to, the organic acids of the general formulas R—COOH, $RSO_2H$, $RSO_3H$, $(RSO_2)NH$, $(RO)_2PO_2H$, ROH where R is a hydrogen or a carbon-containing chain that consists of alkyl or aryl groups, substituted or not by heteroatoms. In a preferred manner, the organic Brønsted acids are selected from among the following organic acids: formic acid, acetic acid, trifluoroacetic acid, lactic acid, levulinic acid, methanesulfinic acid, methanesulfonic acid, trifluoromethanesulfonic acid, bis(trifluoromethanesulfonyl)amine, benzoic acid, paratoluenesulfonic acid, 4-biphenylsulfonic acid, diphenyl phosphate, and 1,1'-binaphthyl-2,2'-diyl hydrogenophosphate.

A very preferred organic Brønsted acid homogeneous catalyst is selected from among methanesulfonic acid ($CH_3SO_3H$) and acetic acid ($CH_3COOH$).

In the case where several homogeneous catalysts that are selected from among the inorganic Brønsted acids and the organic Brønsted acids are used in the process according to the invention, said homogeneous catalysts can be identical or different.

In a preferred embodiment, a single homogeneous catalyst that is selected from among the inorganic Brønsted acids and the organic Brønsted acids is used in the process according to the invention. In the case where a single homogeneous catalyst is used, said homogeneous catalyst is the tungstic acid $H_2WO_4$.

In a very preferred embodiment, no other homogeneous catalyst of a nature different from said homogeneous catalyst or catalysts selected from among the organic Brønsted acids and the inorganic Brønsted acids is used in the process according to the invention. For example, no other homogeneous catalyst, such as the metal salts that are hydrated or not, having for a general formula $M_mX_n.n'H_2O$, is added into said same reaction chamber in which the process according to the invention is implemented.

In accordance with the invention, said heterogeneous catalyst or catalysts comprise(s) at least one metal that is selected from among the metals of groups 6 to 11 and the metals of group 14 of the periodic table and a substrate that is selected from among the perovskites of general formula $ABO_3$ in which A is selected from among the elements Mg, Ca, Sr and Ba, and La, and B is selected from among the elements Fe, Mn, Ti and Zr, the oxides of the elements that are selected from among lanthanum (La), neodymium (Nd) and yttrium (Y), cerium (Ce) and niobium (Nb), by themselves or in a mixture, and the mixed oxides that are selected from among the aluminates of zinc (Zn), copper (Cu), and cobalt (Co), by themselves or in a mixture.

In the case where several heterogeneous catalysts are used in the process according to the invention, said catalysts can be identical or different.

Said metal that is selected from among the metals of groups 6 to 11 and the metals of group 14 of the periodic table of the hetereogeneous catalyst or catalysts according to the invention are preferably selected from among the following metals: Cr, Mo, W, Mn, Tc, Re, Fe, Ru, Os, Co, Rh, Ir, Ni, Pd, Pt, Cu, Ag, Au, Zn, Cd, and Hg, on the one hand, and from among: Ge, Sn and Pb, on the other hand, taken by themselves or in a mixture.

In a preferred manner, said metal is selected from among the metals Mo, W, Re, Ru, Co, Rh, Ir, Ni, Pd, Pt, Cu, on the one hand, and Sn, on the other hand, taken by themselves and in a mixture.

In a very preferred manner, said metal is selected from among the metals Ru, Ir, Ni, Pd, Pt, on the one hand, and Sn, on the other hand, taken by themselves or in a mixture.

In an even more preferred manner, said metal is selected from among the metals Ni, Pt, Ru, on the one hand, and Sn, on the other hand, taken by themselves or in a mixture, and in a very preferred manner from among Pt and Ni, taken by themselves or in a mixture.

According to a preferred embodiment, the mixtures of the following metals are preferred: NiSn, RePt, FePt, SnPt, CuPt, IrPt, CoPt, RhPt, OsPt, RuRe, PdRe, RuSn and RuPt, and in an even more preferred manner, the mixtures of the following metals: NiSn, RePt, RuRe and RuPt.

In the case where the metal of said heterogeneous catalyst or catalysts is selected from among the following noble metals: Ru, Os, Rh, Pd, Pt, Ag, Au, the content of noble metal in said heterogeneous catalyst or catalysts is advantageously between 0.1 and 10% by weight and in a preferred manner between 0.1 and 5% by weight relative to the total mass of said heterogeneous catalyst or catalysts.

In the case where the metal of said heterogeneous catalyst or catalysts is selected from among the non-noble metals, the content of non-noble metal in said heterogeneous catalyst or catalysts is advantageously between 0.1 and 40% by weight and in a preferred manner between 0.1 and 30% by weight, in a very preferred manner between 0.1 and 20% by weight relative to the total mass of said heterogeneous catalyst or catalysts.

The metal or metals of the heterogeneous catalyst or catalysts according to the invention is/are advantageously deposited on a substrate.

In accordance with the invention, said heterogeneous catalyst or catalysts comprise(s) a substrate that is selected from among the perovskites of general formula $ABO_3$, in which A is selected from among the elements Mg, Ca, Sr, Ba and La, and B is selected from among the elements Fe, Mn, Ti and Zr, the oxides of elements selected from among lanthanum (La), neodymium (Nd) and yttrium (Y), cerium (Ce), and niobium (Nb), by themselves or in a mixture, and, preferably, from among lanthanum (La), neodymium (Nd), yttrium (Y), and niobium (Nb), and the mixed oxides that are selected from among the aluminates of zinc (Zn), copper (Cu), and cobalt (Co), by themselves or in a mixture.

Nonlimiting examples of perovskite are: $BaTiO_3$, $SrTiO_3$, $BaZrO_3$, $CaZrO_3$, $SrZrO_3$, $CaMnO_3$, $Ca_2FeO_5$, $LaSrO_3$, $LaMnO_3$.

In a preferred manner, the substrate of said heterogeneous catalyst or catalysts is a perovskite.

In another preferred embodiment, the substrate is cerium oxide.

In a preferred embodiment, said oxides, simple or mixed, are doped by at least one element that is selected from among alkalines, alkaline-earths, and rare earths, by themselves or in a mixture.

In the case where said substrate is selected from among the oxides that are doped by at least one element that is selected from among the alkalines, said doping element is advantageously selected from among the elements: Li, Na, K, Rb, Cs, and preferably from among Li, Na, K.

In the case where said substrate is selected from among the oxides that are doped by at least one element that is selected from among the alkaline-earths, said doping element is advantageously selected from among Be, Mg, Ca, Sr, Ba, and preferably from among: Ca, Sr, Ba.

In the case where said substrate is selected from among the oxides that are doped by at least one element that is selected from among the rare earths, said doping element is advantageously selected from among: La, Ce, Sm, Gd, Y, Pr.

Preferably, the content of doping element, which is selected from among the alkalines, the alkaline-earths, and the rare earths, by themselves or in a mixture, is advantageously between 0.1% and 30% by weight and in a preferred manner between 1 and 20% by weight relative to the total mass of said substrate.

The heterogeneous catalyst according to the invention offers the advantage of being stable under the hydrothermal conditions of the reaction, i.e., conditions combining water and temperature in contrast to the refractory oxides, such as the oxides of aluminum or silicon, for example.

The substrate can, however, undergo a treatment stage whose purpose is to improve its stability under the hydrothermal conditions of the reaction. It is possible to cite, for example, the surface passivation, the deposition of carbon-containing film, and the deposition of oxide.

Preferably, the substrate is used without modification, and its purpose is to improve its stability under the hydrothermal conditions of the reaction.

The heterogeneous catalyst has a specific surface area that is less than 100 $m^2/g$, in a preferred manner between 1 and 70 $m^2/g$, and in a very preferred manner between 1 and 40 $m^2/g$.

The deposition of the metal or metals selected from among groups 6 to 11 and the metals of group 14 of the periodic table on said substrate of the heterogeneous catalyst or catalysts according to the invention in general involves a precursor of the metal or metals. For example, it may involve metal organic complexes, metal salts such as metal chlorides, metal nitrates, metal carbonates.

The introduction of the metal or metals can advantageously be carried out by any technique that is known to one skilled in the art, such as, for example, ion exchange, dry impregnation, impregnation by excess, vapor phase deposition, etc. The introduction of metal can be carried out before or after the forming of the substrate.

The stage for introduction of the metal or metals can advantageously be followed by a heat treatment stage. The heat treatment is advantageously carried out between 300° C. and 700° C., under oxygen atmosphere or air. The heat treatment stage can be followed by a temperature reduction treatment. The reducing heat treatment is advantageously carried out at a temperature of between 150° C. and 600° C. under a stream of hydrogen or under a hydrogen atmosphere.

Preferably, said heterogeneous catalyst or catalysts also undergo(es) an in-situ reduction stage, i.e., in the reactor where the reaction takes place, before the introduction of the reaction feedstock. Said reduction stage can also advantageously be carried out ex-situ.

The heterogeneous catalyst or catalysts used in this invention can be in the form of powder, extrudates, balls, or pellets. The forming can be done before or after the introduction of metal.

The heterogeneous catalyst or catalysts used in this invention is/are characterized by the techniques that are known to one skilled in the art.

Transformation Process

In accordance with the invention, the process for transformation of the feedstock that is selected from among the lignocellulosic biomass and the carbohydrates, by themselves or in a mixture, is implemented in a reaction chamber in the presence of at least one solvent, with said solvent being water by itself or in a mixture with at least one other solvent, under a reducing atmosphere, and at a temperature of between 50° C. and 300° C., and at a pressure of between 0.5 MPa and 20 MPa.

The process is therefore implemented in a reaction chamber that comprises at least one solvent and in which said feedstock is brought into the presence of the catalytic system according to the invention.

In accordance with the invention, the process according to the invention is performed in the presence of at least one solvent, with said solvent being water by itself or in a mixture with at least one other solvent.

According to a preferred embodiment, the process according to the invention is performed in the presence of water in a mixture with at least one alcohol or at least one organic solvent, under subcritical or supercritical conditions.

The alcohols are advantageously selected from among methanol, ethanol, and propanols.

The organic solvents can advantageously be selected from among tetrahydrofuran and ethyl acetate.

In the case where said process according to the invention is performed in the presence of water in a mixture with at least one other solvent, the mixture of solvents comprises a water content by mass that is greater than 5% by weight, and in a preferred manner greater than 30%, and in a very preferred manner greater than 50% relative to the total mass of said mixture.

According to another embodiment, the process according to the invention is performed only in the presence of water.

Preferably, the process according to the invention is performed in the presence of at least one solvent except for the solvents that are selected from among the ionic liquids.

In accordance with the invention, the process for transformation of said feedstock is carried out under a reducing atmosphere, preferably under a hydrogen atmosphere. Hydrogen can be used in pure form or in a mixture.

Preferably, said process according to the invention is performed at a temperature of between 50° C. and 300° C., and in a preferred manner between 80° C. and 250° C., and at a pressure of between 0.5 MPa and 20 MPa, and in a preferred manner between 2 MPa and 20 MPa.

In general, the process can be performed according to different embodiments. Thus, the process can advantageously be implemented intermittently or continuously, for example in a fixed bed. It is possible to operate in a closed reaction chamber or in a semi-open reactor.

Said homogeneous catalysts are advantageously introduced into the reaction chamber at a rate of a quantity that corresponds to a feedstock/homogeneous catalyst(s) ratio by mass of between 1.5 and 1,000, preferably between 5 and 1,000, and in a preferred manner between 10 and 500.

The heterogeneous catalyst or catalysts is/are introduced into the reaction chamber at a rate of a quantity corresponding to a feedstock/heterogeneous catalyst(s) ratio by mass of between 1 and 1,000, preferably between 1 and 500, preferably between 1 and 100, preferably between 1 and 50, and even more preferably between 1 and 25.

The heterogeneous catalyst or catalysts introduced into the reactor can undergo a reducing heat treatment stage before the introduction of the reaction feedstock. The reducing heat treatment is preferably carried out at a temperature of between 150° C. and 600° C. under a stream of hydrogen or under a hydrogen atmosphere.

The feedstock is introduced into the process at a rate of a quantity that corresponds to a solvent/feedstock ratio by mass of between 1 and 1,000, preferably between 1 and 500, and even more preferably between 5 and 100.

If a continuous process is selected, the mass speed per hour (mass/heterogeneous catalyst mass feedstock flow rate) is between 0.01 and 5 $h^{-1}$, preferably between 0.02 and 2 $h^{-1}$.

The Products that are Obtained and their Analysis Method

The products of the reaction of the transformation process according to the invention are mono-oxidized or poly-oxidized compounds. Said mono-oxidized or poly-oxidized compounds are water-soluble.

Said mono-oxidized or poly-oxidized compounds advantageously consist of monosaccharides and their derivatives, oligosaccharides, and also soluble polymers that are advantageously formed by successive combinations of the derivatives of monosaccharides.

Monosaccharide refers to a carbohydrate that has as its composition $C_nH_{2n}O_n$ where n is greater than 2, obtained by total hydrolysis of cellulose, or hemicellulose, or starch. Monosaccharides are simple sugars that are produced by complete depolymerization of cellulose and/or hemicellulose, such as in particular glucose, galactose, mannose, xylose, fructose, etc.

Derivatives of monosaccharides and oligosaccharides refer to products that can be obtained by, for example, dehydration, isomerization, reduction or oxidation:

Sugar alcohols, alcohols, and polyols: in particular cellobitol, sorbitol, anhydrosorbitol, hexanetetrols, hexanetriols, hexanediols, xylitol, pentanetetrols, pentanetriols, pentanediols, erythritol, butanetriols, butanediols, glycerol, 1,3-propanediol, propylene glycol, ethylene glycol, hexanols, pentanols, butanols, propanols, ethanol . . .

Monoketones, polyketones: hydroxyacetone, 2,5-hexanedione . . .

Carboxylic acids and their esters, lactones: formic acid, alkyl formates, acetic acid, alkyl acetates, hexanoic acid, alkyl hexanoates, levulinic acid, alkyl levulinates, lactic acid, alkyl lactates, glutaric acid, alkyl glutarates, 3-hydroxypropanoic acid, 3-hydroxybutyrolactone, γ-butyrolactone, γ-valerolactone Cyclic ethers: for example, tetrahydrofuran (THF), 3-methyltetrahydrofuran (Me-THF) and its positional isomers, 2,4-dimethyltetrahydrofuran and its positional isomers, tetrahydropyran-2-methanol and its positional isomers.

Furans: furan-2,5-dicarboxylic acid, 5-(hydroxymethyl) furfural, furfural . . .

Soluble polymers refer to all of the products that are obtained from the condensation between monosaccharides, oligosaccharides and/or derivatives of monosaccharides.

At the end of the reaction, the reaction medium is sampled and centrifuged. The reaction liquid is then analyzed by high-pressure liquid chromatography (HPLC) by using refractometry for determining the content of products for conversion of the aqueous solution.

The quantities of water-soluble reaction products (monosaccharides and derivatives, oligosaccharides, soluble polymers) are determined by TOC (Total Organic Carbon) analysis, which consists in the measurement of carbon in solution. The quantities of monosaccharides and their derivatives are determined by HPLC analyses.

In the examples below, the perovskite substrates of the heterogeneous catalysts are commercial.

The tungstic acid $H_2WO_4$ that constitutes a homogeneous catalyst, inorganic Brønsted acid according to the invention, is commercial and is used without purification. It can also be denoted $WO_3.H_2O$, or $WO_3.xH_2O$, with x between 1 and 20, x being variable as a function of the degree of hydration of the tungsten oxide $WO_3$.

The hydrochloric acid HCl that constitutes a homogeneous catalyst, inorganic Brønsted acid according to the invention, is commercial and used without purification.

The sulfuric acid $H_2SO_4$ that constitutes a homogeneous catalyst, inorganic Brønsted acid according to the invention, is commercial and used without purification.

The methanesulfonic acid $CH_3SO_3H$ that constitutes a homogeneous catalyst, organic Brønsted acid according to the invention, is commercial and used without purification.

The acetic acid $CH_3CO_2H$ that constitutes a homogeneous catalyst, organic Brønsted acid according to the invention, is commercial and used without purification.

Example 1: Preparation of the Catalysts C1, C2, C3, C4, C5, C6 and C7 that Comprise 0.5% by Weight of Pt on a Perovskite-Type Substrate An aqueous solution of hexachloroplatinic acid $H_2PtCl_6.xH_2O$ at 1.67% by weight of Pt (7.2 ml or 0.120 g of Pt) is added at ambient temperature to the perovskite-type substrate of general formula $ABO_3$ (24 g), previously desorbed under vacuum (1 hour, 100° C.). The mixture is stirred for one hour and then evaporated. The solid that is obtained is then placed in the oven at 110° C. for 24 hours to dry. The solid is calcined under a stream of dry air at the temperature of 500° C. for 4 hours. It is then reduced under a stream of hydrogen at 500° C. for two hours. The catalysts that are obtained contain 0.5% by weight of platinum.

The formulations of the prepared catalysts are summarized in Table 1.

Example 2: Preparation of the Catalyst C8 that Comprises 0.5% by Weight of Pt on an Alumina-Type Substrate An aqueous solution of hexachloroplatinic acid $H_2PtCl_6.xH_2O$ at 0.75% by weight of Pt (16 ml, 0.120 g of Pt) is added at ambient temperature to the alumina-type substrate of formula $Al_2O_3$ (24 g) of crystallographic type γ-$Al_2O_3$, previously desorbed under vacuum (1 hour, 100° C.). The mixture is stirred for one hour and then evaporated. The solid that is obtained is then placed in the oven at 110° C. for 24 hours to dry. The solid is calcined under a stream of dry air at the temperature of 500° C. for 4 hours. It is then reduced under a stream of hydrogen at 500° C. for two hours. The catalysts that are obtained contain 0.5% by weight of platinum.

The formulation of the prepared catalyst is summarized in Table 1.

Example 3: Preparation of the Catalyst C9 that Comprises 10% by Weight of Ni on a Perovskite-Type Substrate An aqueous solution of nickel nitrate at 35% by weight (7.2 ml or 2.5 g of Ni) is added at ambient temperature to the perovskite-type substrate of formula $BaZrO_3$ (24 g) previously desorbed under vacuum (1 hour, 100° C.). The mixture is stirred for one hour and then evaporated. The solid that is obtained is then placed in the oven at 110° C. for 24 hours to dry. The solid is calcined under a stream of dry air at the temperature of 150° C. for 1 hour, then 250° C. for 1 hour, then 350° C. for 3 hours, and finally 450° C. for 4 hours. It is then reduced under a stream of hydrogen at 300° C. for two hours. The catalyst that is obtained contains 10.5% by weight of nickel.

The formulation of the catalyst that is prepared is summarized in Table 1.

TABLE 1

Formulation of Heterogeneous Catalysts C1 to C7 and C8 and C9

| NAME | Composition | $S_{BET}$ Catalyst ($m^2/g$) |
|---|---|---|
| C1 | 0.5% Pt/$BaTiO_3$ | 1 |
| C2 | 0.5% Pt/$SrTiO_3$ | 3 |
| C3 | 0.5% Pt/$CaMnO_3$ | 4 |
| C4 | 0.5% Pt/$CaZrO_3$ | 1 |
| C5 | 0.5% Pt/$SrZrO_3$ | 5 |
| C6 | 0.5% Pt/$BaZrO_3$ | 3 |
| C7 | 0.5% Pt/$LaMnO_3$ | 2 |
| C8 | 0.5% Pt/$Al_2O_3$ | 195 |
| C9 | 10.5% Ni/$BaZrO_3$ | 3 |

Example 4: Transformation of Cellulose Using the Catalysts C1, C2, C3, C4, C5, C6 and C7 (0.5% by Weight of Pt/$ABO_3$) in Combination with a Homogeneous Catalyst $H_2WO_4$ Example 4 relates to the conversion of cellulose from a combination of a heterogeneous catalyst C1 to C7, whose preparation is described in Example 1, and a homogeneous catalyst that consists of an inorganic Brønsted acid $H_2WO_4$ for the production of mono-oxidized and poly-oxidized products.

50 ml of water, 1.3 g of SigmaCell® cellulose, 0.13 g of $H_2WO_4$, and 0.55 g of catalyst under nitrogen atmosphere are introduced into a 100-ml autoclave. Tungstic acid is water-soluble under the operating conditions.

The homogeneous catalyst $H_2WO_4$ is introduced into the reaction chamber at a rate of a quantity corresponding to a feedstock/$H_2WO_4$ ratio by mass=10.

The heterogeneous catalysts are introduced into the reaction chamber at a rate of a quantity corresponding to a feedstock/heterogeneous catalyst ratio by mass=2.5.

Cellulose is introduced into the autoclave at a rate of a quantity that corresponds to a solvent/cellulose ratio by mass=38. A cold pressure of 5 MPa of hydrogen is introduced.

The autoclave is heated to 230° C. and, at temperature, the total pressure in the reactor is 10 MPa. After 12 hours of reaction, the reaction medium is sampled and centrifuged. Samples are already taken during the test and analyzed by high-pressure liquid chromatography (HPLC) by using refractometry for determining the content of products for conversion of the aqueous solution.

The results that are obtained are referenced in Table 2.

TABLE 2

Solubilization of Cellulose and Formation of Humins

| Catalyst | Nature | Solubilization at 12 Hours (%) | Formation of Humins |
|---|---|---|---|
| $H_2WO_4$ | $H_2WO_4$ | 55 | Humins |
| C1 + $H_2WO_4$ | 0.5% Pt/$BaTiO_3$ + $H_2WO_4$ | 77 | No Humins |
| C2 + $H_2WO_4$ | 0.5% Pt/$SrTiO_3$ + $H_2WO_4$ | 68 | No Humins |
| C3 + $H_2WO_4$ | 0.5% Pt/$CaMnO_3$ + $H_2WO_4$ | 63 | No Humins |
| C4 + $H_2WO_4$ | 0.5% Pt/$CaZrO_3$ + $H_2WO_4$ | 89 | No Humins |
| C5 + $H_2WO_4$ | 0.5% Pt/$SrZrO_3$ + $H_2WO_4$ | 88 | No Humins |
| C6 + $H_2WO_4$ | 0.5% Pt/$BaZrO_3$ + $H_2WO_4$ | 99 | No Humins |
| C7 + $H_2WO_4$ | 0.5% Pt/$LaMnO_3$ + $H_2WO_4$ | 72 | No Humins |

The combination of a homogeneous catalyst (tungstic acid) and a heterogeneous catalyst containing platinum deposited on a perovskite substrate, of C1- to C7-type, proves more effective in comparison with the homogeneous catalyst taken by itself.

Accelerated solubilization kinetics is observed starting from the combination of heterogeneous platinum-containing catalyst supported on a perovskite substrate described in Example 1 and tungstic acid relative to the tungstic acid taken by itself.

A total disappearance of the formation of humins from the combination of the heterogeneous platinum-containing catalyst supported on a perovskite substrate described in Example 1 and tungstic acid relative to the tungstic acid taken by itself is observed.

The resulting mixture consists of alcohols such as methanol, ethanol, propanols, butanols, pentanols, butanols, hexanols, polyols such as ethylene glycol, propylene glycol, 1,3-propanediol, butanediols, pentanediols, hexanediols, hexanetriols, glycerol, tetraols, pentitols, hexitols, esters such as valerolactone, ethers such as tetrahydrofurans, anhydroerythritol, anhydroxylitol, isosorbide, 1,4-sorbitan, acids such as lactic acid, and other unidentified products.

At the end of the reaction, the constituent elements of the heterogeneous catalyst are metered in the solution by ICP-MS (inductively coupled plasma mass spectrometry). The quantities of Pt and of the element Zr, Sr, Ca, Ti, Mn or Ba passed into solution are less than 2% of the quantity that is introduced. At the end of the reaction, the catalysts C1, C2, C3, C4, C5, C6 and C7 are isolated and dried in the oven. Their structure is analyzed by X-ray diffraction. They have the same perovskite-type $ABO_3$ structure, before and after reaction. The catalysts as claimed in the invention are therefore stable under hydrothermal conditions of the reaction.

Example 5: Transformation of Cellulose Using the Catalyst C6 (0.5% by Weight of Pt/BaZrO₃) in Combination with Different Homogeneous Catalysts (Compliant)

This example relates to the conversion of cellulose from a combination of catalyst C6, whose preparation is described in Example 1, and different homogeneous catalysts that consist of inorganic and organic Brønsted acids listed in Table 3 for the production of mono-oxidized and poly-oxidized products.

50 ml of water, 1.3 g of cellulose SigmaCell®, x mg of homogeneous catalyst, and 0.55 g of catalyst C6=Pt/BaZrO₃ are introduced into a 100-ml autoclave under a nitrogen atmosphere. The organic and inorganic Bronsted acid homogeneous catalysts are water-soluble under operating conditions. A cold pressure of 5 MPa of hydrogen is introduced.

The autoclave is heated to 230° C., and, at temperature, the total pressure in the reactor is 10 MPa. After 12 hours of reaction, the reaction medium is sampled and centrifuged. Samples are also taken during the test and analyzed by high-pressure liquid chromatography (HPLC) by using refractometry for determining the content of products for conversion of the aqueous solution.

The results that are obtained are referenced in Table 3.

TABLE 3

Solubilization of Cellulose and Formation of Humins

| C6 (Pt/BaZrO₃) + Homogeneous Catalyst | Mass x (mg) | Solubilization at 12 Hours (%) | Formation of Humins |
|---|---|---|---|
| No Homogeneous Catalyst | 0 | 52 | No Humins |
| HCl | 8 | 94 | No Humins |
| H₂SO₄ | 20 | 90 | No Humins |
| CH₃COOH | 13 | 95 | No Humins |
| CH₃SO₃H | 19 | 90 | No Humins |

The combination of a homogeneous catalyst and a heterogeneous catalyst containing platinum deposited on a perovskite C6 substrate proves more effective in comparison with the heterogeneous catalyst taken by itself.

Accelerated solubilization kinetics is observed starting from the combination of the heterogeneous platinum-containing catalyst supported on a perovskite C6 substrate and a homogeneous catalyst relative to the heterogeneous catalyst taken by itself.

At the end of the reaction, the constituent elements of the heterogeneous catalyst are metered in the solution by ICP-MS. The quantities of Pt, Zr and Ba passed into solution are less than 2% of the quantity that is introduced. At the end of the reaction, the catalyst C6 is isolated and dried in the oven. Its structure is analyzed by X-ray diffraction. The catalyst C6 has the same perovskite-type BaZrO₃ structure, before and after reaction. The catalyst C6 according to the invention is therefore stable under the conditions of the reaction.

Example 6: Transformation of Cellulose Using the Catalyst C9 (10.5% by Weight of Ni/BaZrO₃) in Combination with Tungstic Acid (Compliant)

This example relates to the conversion of cellulose from a combination of the catalyst C9 described in Example 3 and a homogeneous catalyst that consists of an inorganic Brønsted acid H₂WO₄ for the production of mono-oxidized and poly-oxidized products.

50 ml of water, 1.3 g of SigmaCell® cellulose, 0.13 g of H₂WO₄, and 0.55 g of catalyst C9=Ni/BaZrO₃ are introduced into a 100-ml autoclave under a nitrogen atmosphere. The tungstic acid is water-soluble under the operating conditions. A cold pressure of 5 MPa of hydrogen is introduced.

The autoclave is heated to 230° C., and, at temperature, the total pressure in the reactor is 10 MPa. After 12 hours of reaction, the reaction medium is sampled and centrifuged. Samples are also taken during the test and analyzed by high-pressure liquid chromatography (HPLC) by using refractometry for determining the content of products for conversion of the aqueous solution.

The results that are obtained are referenced in Table 4.

TABLE 4

Solubilization of Cellulose and Formation of Humins

| Catalysts | Nature | Solubilization at 12 Hours (%) | Formation of Humins |
|---|---|---|---|
| H₂WO₄ | H₂WO₄ | 55 | Humins |
| C9 + H₂WO₄ | 10% Ni/BaZrO₃ + H₂WO₄ | 95 | No Humins |

The combination of tungstic acid and a heterogeneous catalyst C9 containing nickel deposited on a perovskite substrate proves more effective in comparison with the tungstic acid taken by itself.

Accelerated solubilization kinetics is observed starting from the combination of heterogeneous nickel-containing catalyst C9 supported on a perovskite substrate and tungstic acid relative to the tungstic acid taken by itself.

A total disappearance of the formation of humins from the combination of the heterogeneous nickel-containing catalyst C9 supported on a perovskite substrate and tungstic acid relative to the tungstic acid taken by itself is observed.

At the end of the reaction, the constituent elements of the heterogeneous catalyst are metered in the solution by ICP-MS. The quantities of Ni, Zr and Ba passed into solution are less than 2% of the quantity that is introduced. At the end of the reaction, the catalyst C9 is isolated and dried in the stove. Its structure is analyzed by X-ray diffraction. The catalyst C9 has the same perovskite-type $BaZrO_3$ structure, before and after reaction. The catalyst C9 according to the invention is therefore stable under the conditions of the reaction.

Example 7: Transformation of Cellulose Using the Catalyst C8 (0.5% by Weight of $Pt/Al_2O_3$) in Combination with Tungstic Acid (Non-Compliant)

This example relates to the conversion of cellulose from a combination of the catalyst C8, whose preparation is described in Example 2, and a homogeneous catalyst that consists of an inorganic Brønsted acid $H_2WO_4$ for the production of mono-oxidized and poly-oxidized products.

50 ml of water, 1.3 g of SigmaCell® cellulose, 0.13 g of $H_2WO_4$, and 0.55 g of catalyst C8=$Pt/Al_2O_3$ are introduced into a 100-ml autoclave under a nitrogen atmosphere. The tungstic acid is water-soluble under the operating conditions. A cold pressure of 5 MPa of hydrogen is introduced.

The autoclave is heated to 230° C. and, at temperature, the total pressure in the reactor is 10 MPa. After 12 hours of reaction, the reaction medium is sampled and centrifuged. Samples are also taken during the test and analyzed by high-pressure liquid chromatography (HPLC) by using refractometry for determining the content of products for conversion of the aqueous solution.

The results that are obtained are referenced in Table 5.

TABLE 5

Solubilization of Cellulose and Formation of Humins

| Catalysts | Nature | Solubilization at 12 Hours (%) | Catalyst Structure Stability |
|---|---|---|---|
| C6 + $H_2WO_4$ | 0.5% $Pt/BaZrO_3$ + $H_2WO_4$ | 99 | Yes |
| C8 + $H_2WO_4$ | 0.5% $Pt/Al_2O_3$ + $H_2WO_4$ | 80 | No |

After the cellulose is solubilized, the catalysts are isolated and dried in the oven. Their structures are analyzed by X-ray diffraction. The catalyst C8 has a structure of the crystallographic boehmite type, different from its original structure of the crystallographic γ-alumina type. The quantity of Pt measured in solution is 10%. The catalyst C8 is unstable under the reaction conditions. The catalyst C8 is therefore not in accordance with the invention.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The entire disclosures of all applications, patents and publications, cited herein and of corresponding French Application No. 14/59112, filed Sep. 26, 2014 are incorporated by reference herein.

The invention claimed is:

1. A process for transformation of a feedstock that is selected from among a lignocellulosic biomass and carbohydrates, by themselves or in a mixture, into mono-oxidized or poly-oxidized compounds, in which said feedstock is brought into contact, simultaneously, with a catalytic system that comprises one or more homogeneous catalyst(s) and one or more heterogeneous catalyst(s), in the same reaction chamber, in the presence of at least one solvent, with said solvent being water by itself or in a mixture with at least one other solvent, under a reducing atmosphere, and at a temperature of between 50° C. and 300° C., and at a pressure of between 0.5 MPa and 20 MPa, in which said homogeneous catalyst(s) is/are selected from among inorganic Brønsted acids and organic Brønsted acids said heterogeneous catalyst(s) is/are selected from among heterogeneous catalyst(s) comprising: at least one metal that is selected from among the metals of groups 6 to 11 and the metals of group 14 of the periodic table; and a substrate that is selected from among perovskites of formula $ABO_3$, in which A is selected from among elements Mg, Ca, Sr and Ba, and La, and B is selected from among: elements Fe, Mn, Ti, and Zr; oxides of elements selected from among lanthanum (La), neodymium (Nd) and yttrium (Y), cerium (Ce) and niobium (Nb), by themselves or in a mixture; and mixed oxides that are selected from among aluminates of zinc (Zn), copper (Cu), and cobalt (Co), by themselves or in a mixture.

2. The process according to claim 1, in which said feedstock is brought into contact simultaneously with a catalytic system that consists of said homogeneous catalyst(s) and said heterogeneous catalyst(s).

3. The process according to claim 1, in which the homogeneous catalyst(s) is/are selected from among the inorganic Brønsted acids, which are selected from among the following inorganic acids: HF, HCl, HBr, HI, $H_2SO_3$, $H_2SO_4$, $H_3PO_2$, $H_3PO_4$, $HNO_2$, $HNO_3$, $H_2WO_4$, $H_4SiW_{12}O_{40}$, $H_3PW_{12}O_{40}$, $(NH_4)_6(W_{12}O_{40}) \cdot xH_2O$, $H_4SiMo_{12}O_{40}$, $H_3PMo_{12}O_{40}$, $(NH_4)_6Mo_7O_{24} \cdot xH_2O$, $H_2MoO_4$, $HReO_4$, $H_2CrO_4$, $H_2SnO_3$, $H_4SiO_4$, $H_3BO_3$, $HClO_4$, $HBF_4$, $HSbF_5$, $HPF_6$, $H_2FO_3P$, $ClSO_3H$, $FSO_3H$, $HN(SO_2F)_2$ and $HIO_3$.

4. The process according to claim 3, in which the inorganic Brønsted acids are selected from the following inorganic acids: HCl, $H_2SO_4$, $H_3PO_4$, $H_2WO_4$, $H_2MoO_4$, $HReO_4$, and $H_2CrO_4$.

5. The process according to claim 4, in which the inorganic Brønsted acid is tungstic acid $H_2WO_4$.

6. The process according to claim 1, in which the homogeneous catalyst(s) is/are selected from among the organic Brønsted acids, which are selected from among organic acids of the formulas R—COOH, $RSO_2H$, $RSO_3H$, $(RSO_2)NH$, $(RO)_2PO_2H$, and ROH where R is a hydrogen or a carbon-containing chain that consists of alkyl or aryl groups, substituted or not by heteroatoms.

7. The process according to claim 6, in which the organic Brønsted acids are selected from among formic acid, acetic acid, trifluoroacetic acid, lactic acid, levulinic acid, methanesulfinic acid, methanesulfonic acid, trifluoromethanesulfonic acid, bis(trifluoromethanesulfonyl)amine, benzoic acid, paratoluenesulfonic acid, 4-biphenylsulfonic acid, diphenyl phosphate, and 1,1'-binaphthyl-2,2'-diyl hydrogenophosphate.

8. The process according to claim 7, in which the organic Brønsted acid is selected from among methanesulfonic acid and acetic acid.

9. The process according to claim 1, in which the metal of the heterogeneous catalyst or catalysts is selected from among the metals Mo, W, Re, Ru, Co, Rh, Jr, Ni, Pd, Pt, Cu and Sn, taken by themselves and in a mixture.

10. The process according to claim 9, in which the metal of the heterogeneous catalyst or catalysts is selected from among the metals Ni, Pt, Ru and Sn, taken by themselves or in a mixture.

11. The process according to claim 1, in which the homogeneous catalysts are introduced into the reaction chamber at a rate of a quantity that corresponds to a feedstock/homogeneous catalyst(s) ratio by mass of between 1.5 and 1,000.

12. The process according to claim 1, in which the solvent is water only.

13. The process according to claim 1, in which the reducing atmosphere is a hydrogen atmosphere, pure or in a mixture.

14. The process according to claim 1, operating at a temperature of between 80° C. and 250° C., and at a pressure of between 2 MPa and 20 MPa.

* * * * *